Oct. 11, 1932. M. A. BLAKE Plant Pat. 31
PEACH
Filed Dec. 31, 1931
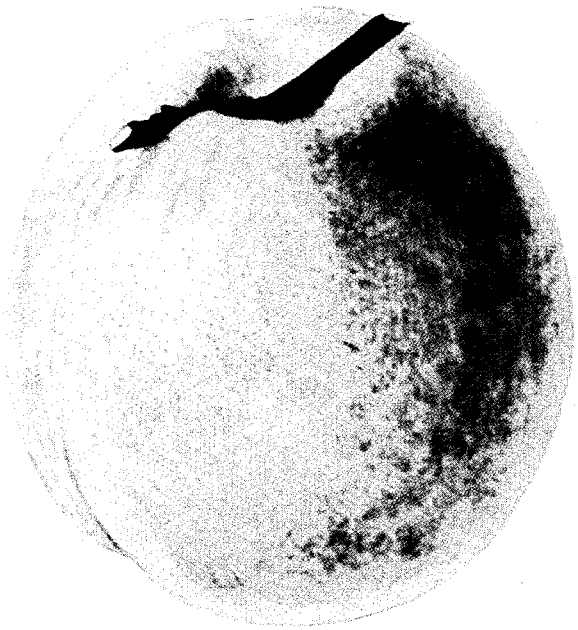
INVENTOR
M. A. BLAKE
BY Robb & Robb
M. P. Macdonald
ATTORNEYS Patented Oct. 11, 1932

Plant Pat. 31

UNITED STATES PATENT OFFICE

MAURICE A. BLAKE, OF NEW BRUNSWICK, NEW JERSEY, ASSIGNOR TO NEW JERSEY STATE AGRICULTURAL EXPERIMENT STATION, OF NEW BRUNSWICK, NEW JERSEY

PEACH

Application filed December 31, 1931. Serial No. 584,206.

The present invention relates to a new and distinct variety of peach, primarily characterized as to novelty by the color of the flesh of its fruit and the lateness of the ripening of the same compared with other fruit possessing any similar characteristics.

The seed parent of this variety was the J. H. Hale, probably open-pollinated by Ray. The fruit closely resembles that of the J. H. Hale in form but not in color of the flesh, as above indicated.

The tree is of a vigorous spreading habit with large vigorous leaves and reniform glands.

The bloom of this variety is of the medium petal type, somewhat like Belle and Elberta. An important characteristic of the bloom is that it is perfect and self fertile and not sterile like the J. H. Hale.

It is in connection with the fruit that this variety is particularly distinguishable. The fruit has much the same shape as the seed parent, is large, round, white fleshed, differing from all other white fleshed varieties in that it is not only round and white fleshed with red around the pit, but the flesh is more firm, the pubescence is shorter, and the characteristic splashing of dull red color, combined with a pit or stone that has coarse corrugations and markings that make the combination differ from that of any white peach.

As shown in the drawing the white undercolor is splashed and marked with dull red. The dull red splashings of color appear where the fruit is exposed to light, except in some cases where the fruit becomes solidly covered with red when the dull markings become inconspicuous.

Another important distinction of this variety resides in the season of ripening. It ripens at the same season as the standard variety J. H. Hale, grown, of course, under comparable conditions. No other named or cultivated variety similar to it in fruit characteristics ripens at this season, there being no other white fleshed J. H. Hale now in existence, as far as known.

For purposes of convenience I summarize the characteristics of this new variety of peach as follows:

*Tree.*—Large, vigorous, spreading, twigs medium thick.

*Leaves.*—Large, rather flat sometimes, slightly folded upward, glands reniform.

*Flower buds.*—Medium large, oval, plump pubescent.

*Flowers.*—Pink, of the medium petal type, and about 1 inch or a little more in diameter.

*Fruits.*—Regular in form, round to roundish oval; cavity, deep, wide; suture shallow, sometimes merely a line upon the side; apex well rounded with a small point slightly depressed; skin color greenish white to cream white, completely overspread with red where fully exposed to the sun with coarse splashings of color sometimes discernible; slightly shaded areas show fine dots of light red. The fruit is also marked with narrow splashes of dull red where areas of red color adjoin portions showing little red color. Upon very highly colored areas, the dull red markings may be almost obscured by the brighter red; pubescense light and quite short; flesh white, firm, juicy, sprightly, good quality, red about the pit, stone free with rather coarsely grooved and pitted surface.

I claim:

The peach tree herein described, characterized by the self fertile peculiarity of its flower, and the white fleshed characteristic, the color and ripening season of its fruit, as shown.

In testimony whereof, I affix my signature.

MAURICE A. BLAKE.